United States Patent [19]

Kamen

[11] Patent Number: 4,786,800
[45] Date of Patent: Nov. 22, 1988

[54] FLUID DROP DETECTION AND DISCRIMINATION SYSTEM

[75] Inventor: Dean L. Kamen, Bedford, N.H.

[73] Assignee: Baxter International Inc., Deerfield, Ill.

[21] Appl. No.: 72,564

[22] Filed: Jul. 13, 1987

Related U.S. Application Data

[63] Continuation-in-part of Ser. No. 680,487, Dec. 11, 1984, Pat. No. 4,680,462.

[51] Int. Cl.$^4$ .............................................. G01V 9/04
[52] U.S. Cl. ................................. 250/222.1; 604/253
[58] Field of Search ................. 250/221, 222.1, 222.2, 250/561, 564, 565; 356/436, 437; 604/253

[56] References Cited

U.S. PATENT DOCUMENTS 4,498,901  2/1985  Finch .............................. 604/253 X
4,680,462  7/1987  Kamen ............................. 250/222.1

Primary Examiner—Eugene R. LaRoche
Assistant Examiner—Steven J. Mottola
Attorney, Agent, or Firm—Mary R. Jankousky; Paul C. Flattery; Bruce D. Sunstein

[57] ABSTRACT

A system and method is provided for detecting the presence of drops in a fluid drop path, such as that in a medical infusion system, and for discriminating between signals resulting from true drops and signals resulting from aberrant fluid flow. A transducer generates a drop signal related to the presence of a drop in a fluid drop path. Also generated is a reference quantity related to the value of the drop signal in the absence of a drop. The deviation of the drop signal from the reference quantity is calculated, and is compared with first and second threshold values. The results of these two comparisons are then used to determined the presence or absence of a true drop.

12 Claims, 3 Drawing Sheets

FLUID DROP DETECTION AND DISCRIMINATION SYSTEM

The present application is a continuation-in-part of Ser. No. 680,487, filed on Dec. 11, 1984, now U. S. Pat. No. 4,680,462, which issued on July 14, 1987.

BACKGROUND OF THE INVENTION

1. Technical Field

The present invention relates to devices for detecting the presence of a drop in a drip chamber or similar structure in a medical infusion system. In particular, the invention relates to detection devices of the type utilizing an electrically powered light source and a corresponding photoelectric transducer.

2. Background Art

It is known in the art to use a light source, such as a light-emitting diode, coupled with a phototransducer, such as a phototransistor, to monitor a drop path such as that found in a medical infusion system. There are several known problems in designing such a detector, due to the environment in which it must operate. Typically, a drop of fluid does not cause a large change in the detection beam relative to the intensity of the beam, thus producing a signal that can be difficult to interpret. Further, a detection system must be operable in an extremely wide range of ambient light conditions, and must take into account variations from drip chamber to drip chamber and the occurrence of misting, droplet formation and other time-varying conditions. These factors may give rise to spurious signals, as well as causing light levels to potentially fall outside of the optimal operating ranges of the detection system.

A variety of approaches to this problem are reflected in the art. U.S. Pat. No. 4,321,461, issued for an invention of Walter et al., discloses a system using a pulsed infra-red radiation emitter-and-receiver pair including a phototransistor. Negative feedback is provided to stabilize the system. A pulse system in a device for detection of emboli is disclosed in U.S. Pat. No. 4,280,495, issued for an invention of Lampert. U.S. Pat. No. 4,314,484, issued for an invention of Bowman, discloses another feedback system used to stabilize a light detection device by regulating the output of the light emitter.

SUMMARY OF THE INVENTION

The present invention provides a system and method for detecting the presence of drops in a fluid drop path; the present invention further provides a system and method for discriminating between signals resulting from true drops and signals resulting from aberrant fluid flow.

In a preferred embodiment, a transducer generates a drop signal related to the presence of a drop in a fluid drop path. Also generated is a reference quantity related to the value of the drop signal in the absence of a drop. The deviation of the drop signal from the reference quantity is calculated, and is compared with first and second threshold values. The results of these two comparisons are then used to determine the presence or absence of a true drop.

In other preferred embodiments, an automatic gain control is provided for the system, and system outputs are connected to a microcontroller to provide additional control and/or alarm functions.

DESCRIPTION OF SPECIFIC EMBODIMENTS

Figure 1A:
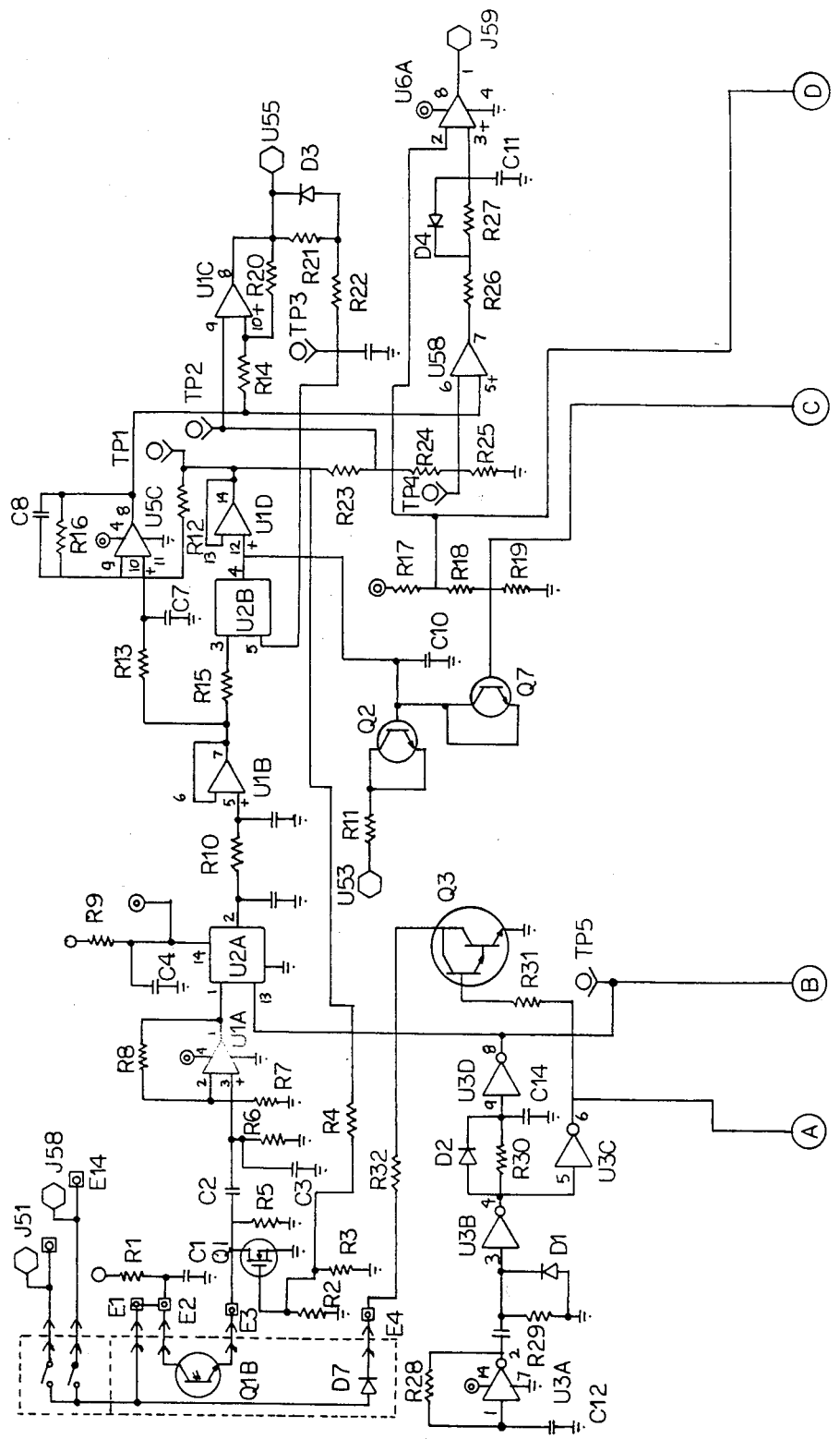
FIGS. 1a, 1b and 1c are schematic diagrams of a preferred embodiment of a drop detection and discrimination system according to the present invention.
Figure 1B:
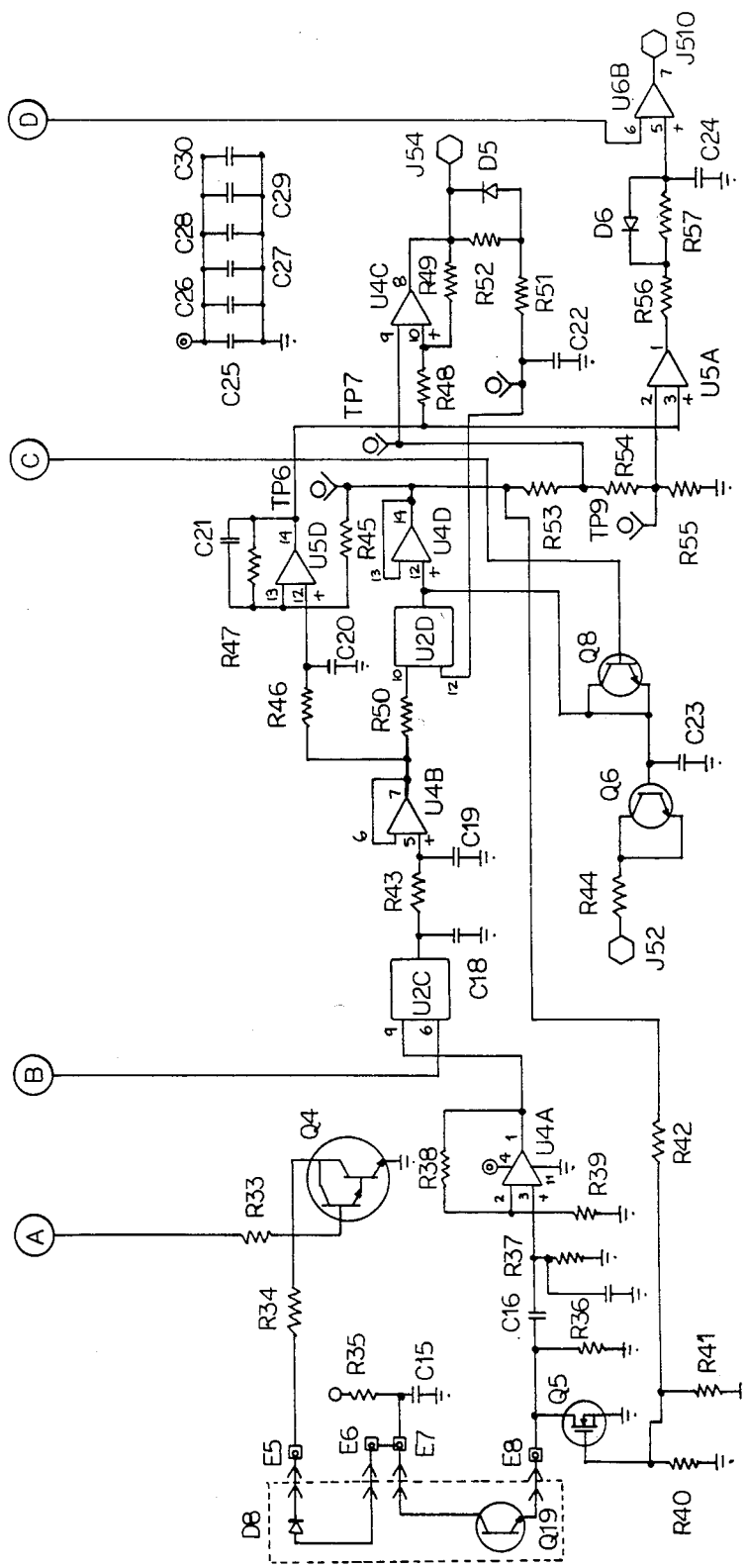
Figure 1C:
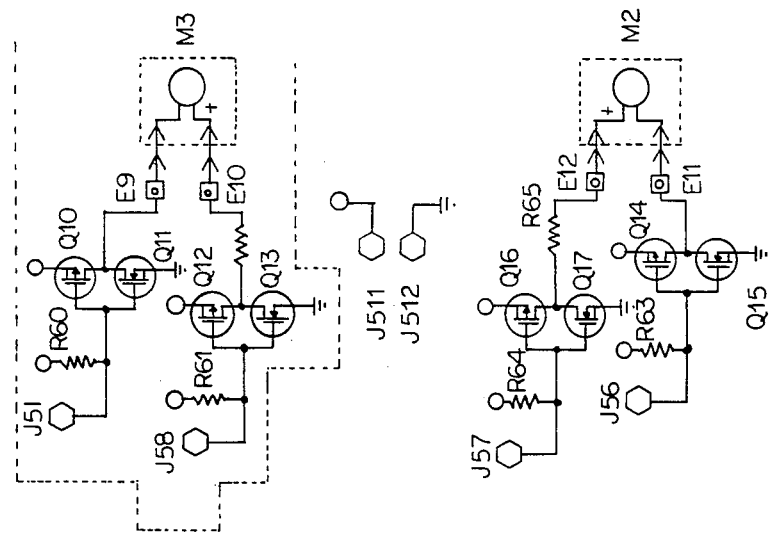

The present drop detection and discrimination system may be further understood with respect to the preferred embodiment depicted in FIG. 1.

Light emitting diode D7 and photodiode Q18 are disposed adjacent to a fluid drop path such as that in a medical infusion system. LED D7 and photodiode Q18 are so arranged about the path that the movement of a drop along the path produces a drop signal at Q18 arising from the drop's occlusion of light from LED D7. In the present embodiment, the path of light from LED D7 to photodiode Q18 is substantially perpendicular to the fluid drop path. A suitable illumination arrangement for use with the present invention is set forth in U.S. Pat. No. 4,673,820, which issued on June 16, 1987, for an invention by Kamen, the inventor in the present case.

The drop signal is filtered by high-pass filter R5/C2, and low-pass filter R6/C3, and is then amplified by operational amplifier U1-A, which is one section of a four-section operational amplifier, such as type TLC274CD. In the present embodiment, op-amp U1-A is configured with resistors R7 and R8 to provide a non-inverted gain of approximately 20.

It will be seen that LED D7 is driven by a pulse generator via Darlington pair Q3. The pulse generator is a relaxation oscillator circuit associated with Schmidt inverter-buffers U3-A, U3-B, U3-C, and U3-D, which are each sections of a six-section device of the type 74C914. The values of the components of the pulse generator have been chosen to produce a 900 Hz, 30-microsecond pulse through photodiode D7, and a 900 Hz, 15-microsecond pulse into the control input of U2-A, delayed 15 microseconds from the start of the 30-microsecond pulse through photodiode D7. The 15-microsecond delay permits transients in the system to die down before gate U2-A starts to conduct.

The use of a pulse generator is desirable because it serves to reduce the power requirements of the system, and further serves to prevent over-illumination of the intravenous fluid, which may be photosensitive. However, it would be possible within the spirit of the invention to eliminate the pulse generator and use continuous illumination of the drop path.

The drop signal is integrated by RC network C5/R10/C6. Voltage follower U1-B then presents the amplified and filtered drop signal for comparison with a reference voltage in order to determine whether a "drop" has occurred, and whether that drop is a "true" drop. The reference voltage is the drop signal level before the detection of a drop.

Through experimentation, it has been determined that a decrease of more than approximately 6 percent of the drop signal relative to the reference voltage indicates that a "drop" has occurred, i.e., that there has been a sufficient occlusion of the detection beam to indicate that a significant amount of fluid has entered the drop path.

It has further been determined that a decrease of more than approximately 10 percent of the drop signal, relative to the reference voltage, occurring 32 milliseconds after the detection of the drop indicates that the drop in the drop path is, in fact, a "true" drop, i.e., a drop having the requisite physical characteristics (e.g., size, shape, volume) to cause a deviation in the system input of about 10 percent with respect to the reference input. Other embodiments described herein analyze the occurrence of true and "false" drops to detect various abnormal or spurious conditions. The specific thresholds of 6 and 10 percent and the time separating them may change depending on the physical characteristics of the infused liquid, such as surface tension or viscosity. The skilled artisan may vary these parameters as necessary.

It will be appreciated that any threshold is in fact somewhat arbitrary, in that too low a threshold risks spurious responses and too high a threshold risks a failure of detection of drops. The present invention combines in a preferred embodiment a relatively low first threshold with a relatively higher second threshold, and makss a condition of detection of a true drop that the second threshold has been exceeded. In this way, the second threshold guarantees that the drop signal detected with the lower threshold is in fact "clean" enough that the second threshold has also been exceeded. If the second threshold is not exceeded, the system can alert the user that the drop signal has become marginal, so that corrective action can be taken. In addition, the use of a time delay between the threshold determinations further helps to assure that, when the second threshold is exceeded, a true drop is present.

The reference voltage is established and maintained by gate U2-B operating in conjunction with resistor R15, capacitor C10 and voltage follower U1-D. It will be seen that U2-B conducts so long as the voltage at control input 5 is high, which is the output of U1-C where no drop has been detected, as explained further below. Thus, in the absence of a drop the reference voltage floats to reflect ambient light levels, subject to the automatic gain control reset, described below.

When a drop is detected, the control input voltage goes low. Gate U2-B no longer conducts, thus preventing the drop signal from affecting the reference voltage, which is maintained by capacitor C10. The values of resistor R15 and C10 are chosen to introduce a relatively large time constant into the movement of the reference voltage. This relatively large time constant permits the system to detect a drop, as explained below, well before the drop signal affects the reference voltage.

At op-amp U5-C, the reference voltage is compared with the present drop signal, which has been filtered by low-pass filter R13/C7. Op-amp U5-C is configured with feedback RC network R16/C8 and with resistors R2, R3, R4, R12, R16, R23, R24, and R25 to produce a filtered amplified gain of approximately 5.25. Thus, the output of op-amp U5-C is a deviation signal that is equal to 5.25 x (drop signal voltage—reference voltage).

The deviation signal is then compared with two threshold voltages at comparators U1-C and U5-B. It will be seen that the threshold voltages are determined by the resistor network R23/R24/R25, which divides the reference voltage. Based on the values R23=300K, R24=220K, and R25=430K, it is apparent that the first threshold for comparison is approximately 0.32 x reference voltage, and the second threshold is approximately 0.55 x reference voltage.

Thus, comparator U1-C will go low when the present drop signal decreases to below roughly 94 percent of the reference voltage, and comparator U5-B will go low when the present drop signal decreases to below roughly 90 percent of the drop signal. This means that comparator U1-C will generate a signal whenever there has been an occlusion of the drop path causing a rapid 6-percent decrease in the light level at photodiode Q18, and comparator U5-B will generate a signal whenever there has been an occulsion of the drop path causing a rapid 10 percent decrease in the light level at photodiode Q18.

Comparators U1-C and U5-B generate digital signals at nodes J5-5 and J5-9, which can serve as inputs to a microprocessor. In the present embodiment, it is contemplated that the signals will be processed by a microcontroller, such as the 80C31. The use of resistors R21, R22, R26, and R27, diodes D3 and D4, capacitor C11 and comparator U6-A are dictated by the signal requirements of the particular microcontroller chosen, and may be adapted as required for other digital signal processors.

The output of comparator U1-C is connected via the low-pass filter R22/C9 to the control input of gate U2-B. Thus, as discussed above, when the U1-C output goes high, as is the condition in the absence of a drop, gate U2-B conducts so as to allow the present drop signal to establish a reference voltage. As further discussed above, capacitor C10 maintains the reference voltage when gate U2-B is not conducting, i.e., when a drop has been detected.

Suggested values for the components of the system are set forth in the following table:

TABLE I

| R1 = 68 | R17 = 100K | C1 = 1000 μF |
|---|---|---|
| R2 = 8.2K | R18 = 100K | C2 = .022 μF |
| R3 = optional | R19 = 100K | C3 = .01 μF |
| R4 = 10K | R20 = 1 M | C4 = 22 μF |
| R5 = 470 | R21 = 680K | C5 = .001 μF |
| R6 = 10K | R22 = 4.7K | C6 = 100 pF |
| R7 = 100K | R23 = 300K | C7 = .001 μF |
| R8 = 2.2 M | R24 = 220K | C8 = .001 μF |
| R9 = 68 | R25 = 430K | C9 = .1 μF |
| R10 = 100K | R26 = 4.7K | C10 = .27 μF |
| R11 = 100 | R27 = 3.3 M | C11 = .022 μF |
| R12 = 220K | R28 = 300K | C12 = .0022 μF |
| R13 = 220K | R29 = 22K | C13 = .001 μF |
| R14 = 4.7K | R30 = 100K | C14 = 100 pF |
| R15 = 4.7 M | R31 = 4.7K | |
| R16 = 1 M | R32 = 10 | |

In addition to its use as the basis upon which the threshold comparisons are made, the reference voltage also provides the basis for a novel automatic gain control. It is known that there is a wide variation in the amplitude of drop signals, due to changes in ambient light. The automatic gain control provided in prior art systems would tend to reduce the signal-to-noise ratio, because these systems are unable to distinguish between changes in signal due to changes in ambient light and changes due to the entrance of a drop into the fluid path. However, in the present system, the basis of the automatic gain control is the reference voltage rather than the signal voltage. Thus, the overall system gain is adjusted by the automatic gain control only in response to changes in the reference voltage.

In the present embodiment, automatic gain control is provided by feeding the reference voltage back to the incoming drop signal via field-effect transistor Q1. As configured, FET Q1 inverts the reference voltage signal, thus producing the necessary negative feedback.

The automatic gain control will thus adjust the gain of the system when there are changes in the level of the reference voltage arising from such ordinary phenomena as changes in ambient light due to turning a room light on or off, or the transition between daytime and nighttime. The automatic gain control will also adjust the gain of the system when there is a change in the reference voltage resulting from splashed liquid residing on the wall of the drip chamber within the path of the light beam. Significantly, the choice of using the reference voltage for the automatic gain control herein prevents the gain from being reduced during the presence of a light signal that is determined to be a drop. The automatic gain control signal remains unchanged when a drop is present, so that the drop signal is preserved at its full magnitude relative to the reference voltage.

The present embodiment further provides a means of resetting the reference voltage maintained on capacitor C10, which would be necessary in the even of streaming, phototransducer failure, or other event resulting in a sustained signal reduction. Such a resetting operation is initiated from an input at node J5-3. The node J5-3 is momentarily grounded, thereby reducing the voltage impressed upon C10 by allowing current to flow through transistor Q2 and resistor R11 to ground.

As discussed above, the system outputs at nodes J5-5 (6-percent deviation) and J5-9 (10-percent deviation) are preferably connected to a microcontroller, such as the 80C31. In operation, a low output at J5-5 will trigger an interrupt, and the microcontroller will enter into a time delay subroutine. It has been determined that that 32 milliseconds is an appropriate delay. At the expiration of the delay, the microcontroller reads the output at J5-9 to determine if the drop is a true drop. This method of interrupt-delay-read can be used as an alternative to continuous monitoring of the system outputs.

The microcontroller can also be programmed with various alarms responsive to the system outputs. For example, assuming a 6-percent deviation is present for all drops, if a 10-percent deviation is not present for five drops in a row or not for five drops out of twenty-five, an alarm will be triggered. Another preferred alarm program code responds to a "flurry," i.e., a rapid succession of drops which often occurs just prior to streaming. In this case, if a specified number, in this embodiment nine, of interrupts are received from the output at J5-5 during the time delay (i.e., before the output at J5-9 is read), an alarm signal is triggered.

In the present embodiment, a secondary drop detector is placed in tandem with the primary drop detector, and driven by the same pulse generator. It will be seen that each element in the primary detector has a correlative element in the secondary detector.

What is claimed is:

1. A drop detection and discrimination system, comprising:
    drop signal generation menas for generating an ongoing drop signal of varying levels related to the presence or absence of a drop in a fluid drop path;
    reference menas for generating a reference quantity related to the drop signal level in the absence of a drop;
    comparison means for comparing the current drop signal level and the reference quantity and generating a deviation quantity related to the difference between the drop signal level and the reference quantity;
    comparison means for comparing the deviation quantity both with a first threshold indicative of the presence of a drop and with a relatively higher second threshold determinative of the presence or absence of a true drop.

2. The system according to claim 1, wherein the reference means is in communication with the drop signal generation means, and the reference means further includes storage means for storing a value indicative of the drop signal level in the absence of a drop.

3. The system according to claim 2, further comprising gating means for gating off the reference means from the drop signal generation means when a drop is detected.

4. The system according to claim 3, wherein the gating means is responsive to the comparison means.

5. The system according to claim 1, further comprising automatic gain control means for controlling the gain of the system in response to different levels of the reference quantity.

6. The system according to claim 1, wherein the comparison means includes means for comparing the deviation quantity with the second threshold value at a predetermined amount of time after the deviation quantity has exceeded the first threshold value.

7. The system according to claim 6, wherein the predetermined amount of time is approximately 32 milliseconds.

8. The system according to claim 1 further including first threshold determination means for determining the first threshold as a first predetermined fractional quantity of the reference quantity.

9. The system according to claim 8, wherein the first fractional quantity is substantially equal to 94 percent.

10. The system according to claim 9 further including second threshold determination means for determining the second threshold as a second predetermined fractional quantity of the reference quantity.

11. The system according to claim 10, wherein the second fractional quantity is substantially equal to 90 percent.

12. A method for detecting and discriminating among drops in a fluid drop path, comprising the steps of:
    generating an ongoing drop signal of varying levels indicative of the presence or absence of a drop in the drop path;
    storing a reference quantity related to the drop signal level in the absence of a drop in the drop path;
    comparing the current drop signal level with the reference quantity;
    generating a "drop in" signal when the drip signal drops below a first predetermined threshold percentage of the reference quantity;
    generating a "drop OK" signal when the drop signal drops below a second predetermined threshold percentage of the reference quantity at a predetermined time after a "drop in" signal has been generated.

* * * * *